United States Patent [19]

Frenkel et al.

[11] Patent Number: 4,473,549
[45] Date of Patent: Sep. 25, 1984

[54] **METHOD FOR THE IMMUNIZATION OF ANIMALS AND MEN AGAINST *TOXOPLASMA GONDII***

[75] Inventors: Jacob K. Frenkel, Overland Park, Kans.; Elmer R. Pfefferkorn, 24 Rope Ferry Rd., Hanover, N.H. 03755

[73] Assignees: The Kansas University Endowment Association; Elmer R. Pfefferkorn, ; a part interest

[21] Appl. No.: 403,787

[22] Filed: Jul. 30, 1982

[51] Int. Cl.³ .................................. A61K 39/002
[52] U.S. Cl. .............................. 424/88; 424/93
[58] Field of Search ............... 424/88, 92, 93, 89

[56] References Cited

PUBLICATIONS

Frenkel, J. K., Toxoplasmosis: Parasite Life Cycle, Pathology and Immunity, pp. 344–377, 1973.
Frenkel, J. K., Annals New York Academy of Sciences, vol. 64, pp. 215–251, 1956.
Pfefferkorn, E. R., et al., Experimental Parasitology, vol. 39, pp. 365–376, 1976.
Remington, J. S. et al., Immunology of Parasitic Infections, Blackwell Scientific Publications, pp. 259–263, 1976.
Krahenbuhl, J., et al., J. Immunology, vol. 108, pp. 425–431, 1972.
Seah, S., et al., Can. J. Microbiol., vol. 21, pp. 1379–1385, 1975.
Chhabra, M., et al., Int. J. Radiat. Biol., vol. 35, pp. 433–440, 1979.
Tran Manh Sung, R., et al., Irradie A Dose Lethale Ou Infra-Lethale Par Des Rayons Gamma, vol. 245, pp. 163–167, 1981.
Mas Bakal, P., et al., Z. Parasitenkd., vol. 59, pp. 211–217, 1979.
Grimwood, Brian G., Infection and Immunity, vol. 28, pp. 532–535, 1980.
Araujo, F., et al., Immunology, vol. 27, pp. 711–721, 1974.
Swartzberg, J., et al., Infection and Immunity, vol. 12, pp. 1037–1043, 1975.
Dubey J., J. Protozool., vol. 25, pp. 382–384, 1978.
Dubey J., Am. J. Vet. Res., vol. 42, pp. 2068–2070, 1981.

*Primary Examiner*—Blondel Hazel
*Attorney, Agent, or Firm*—Schmidt, Johnson, Hovey & Williams

[57] ABSTRACT

A method for the immunization of mammals (including man) and birds, against *Toxoplasma gondii* is described which involves subcutaneous administration of a live, low-virulent vaccine comprising a temperature-sensitive mutant of the persistent, virulent RH strain of *T. gondii*. The vaccine gives immunity against subsequent challenge, but does not persist and does not cause chronic infection of the subject and which therefore cannot result in illness or death in the event that the subject later becomes immunosuppressed.

3 Claims, No Drawings

METHOD FOR THE IMMUNIZATION OF ANIMALS AND MEN AGAINST *TOXOPLASMA GONDII*

BACKGROUND OF THE INVENTION

1. Field of the Invention

The present invention is concerned with a method for immunizing animals of various types against *Toxoplasma gondii*. More particularly, it is concerned with such a method which makes use of a specific mutant of *T. gondii* which has surprisingly been found to give immunity without concomitant chronic infection of the animal.

2. Description of the Prior Art

Toxoplasmosis is an animal disease that can be transmitted to man, typically through contact with cat feces or raw meat. The disease is common to all domestic animals, including barnyard species. Ultimately, however, the possibility of human infection presents the most serious problem.

The spectrum of human disease due to Toxoplasma was characterized by a combination of serologic, immunologic and epidemiological studies, and by isolation of Toxoplasma. In the acute infection where cells are destroyed by rapidly proliferating organisms, there may occur fever, pneumonia, an inflammation of the heart muscle, liver and skin (rash). Toward the end of this period or following a subclinical acute infection, localized or generalized swelling of lymph nodes is observed, especially in women. In newborn infants infected in utero, a subacute disease picture is typical. This results from the attenuation of the disease process by the passive immunization conferred by the mother, and the slow acquisition of active immunity due to immaturiy of the fetus and the newborn. In addition to the symptoms of acute Toxoplasmosis mentioned above, meningoencephalitis ("brain fever"), often with hydrocephalus ("water on the brain"), and retinochoroiditis (intraocular inflammation) are important. Most of the mothers who have given birth to infected babies had asymptomatic infections.

Thus, Toxoplasmosis deserves special attention because of the serious danger it raises for the unborn human baby. A pregnant woman may have the infection and unknowingly infect the fetus. Even if diagnosed and treated, the child may be born with permanent brain and eye damage. Diagnosis during pregnancy is uncertain at best and treatment uncertain and risky. For this reason, efforts to prevent infection during pregnancy are important.

It has been known in the past that mammals can be immunized against Toxoplasmosis. The procedure is very typical, and involves administration of a strain of the organism so that the mammal can build up immunity accompanied by specific antibodies against subsequent *T. gondii* challenge. This straightforward procedure presents a number of problems. For example, primary infection of cats (an important carrier of Toxoplasma) is usually followed by oocyst shedding before buildup of immunity. This phenomenon largely defeats the purpose of immunization, in that infective oocysts in the cat feces are a prime carrier of the disease. Furthermore, all known strains of the organism used for primary infections of mammals, while effective for purposes of building up immunity, tend to persist in the mammal for a long period of time, and possibly for a lifetime, with the result that the mammal is chronically infected. This in turn raises the possibility that if such a mammal becomes immunosuppressed later in life, the infection may reactivate with debilitating or even fatal results.

There is therefore a decided and heretofore unsatisfied need for a method of immunizing animals against *T. gondii* which on the one hand gives an adequate level of immunity, but on the other does not persist and cause chronic infection in the animal.

SUMMARY OF THE INVENTION

The present invention overcomes the problems noted above, and provides a method of immunizing animals selected from the group consisting of man, cattle, sheep, goats, birds and zoo mammals (e.g., members of the cat family, new-world monkeys and kangaroos) against *Toxoplasma gondii*. The method involves subcutaneously administering to the animal an amount of a low-virulent mutant of *T. gondii* discovered to have the ability to develop in the animal an immunity to subsequent challenge. Moreover, this immunity is developed without concomitant chronic *T. gondii* infection in the animal.

The mutant particularly found useful in connection with the invention is described in "*Toxoplasma gondii:* Isolation and Preliminary Characterization of Temperature-sensitive Mutants" by E. R. Pfefferkorn et al., *Experimental Parasitology,* Volume 39, pages 365–376 (1976), as the "ts-4" mutant. The above paper is hereby expressly incorporated by reference herein. In addition, a publicly available frozen inoculum of the "ts-4" mutant described in the referenced paper has been deposited with The American Type Culture Collection, Rockville, Md. This culture has been designated "ts-4", and has an accession number of 40050.

The *T. gondii* mutant in accordance with the invention is usually subcutaneously administered in the form of a vaccine, using a saline solution as carrier. Inasmuch as the mutant is injected live, the amount injected is not critical; however, it is believed that a level of at least about 20 tachyzoites of the mutant should be injected. In certain cases multiple vaccinations have proved helpful in assuring complete immunity.

DESCRIPTION OF THE PREFERRD EMBODIMENTS

Production and Selection of *Toxoplasma gondii* Mutant

1. Materials and Methods

All tissue culture experiments were done with human diploid foreskin fibroblasts in their 15th to 35th passage. These cells were grown in Eagle's (Eagle, H., "Nutritional needs of mammalian cells in tissue culture", *Science* 122, pp. 501–504 (1955)) minimal essential medium containing Earle's (Earle, W. R., "Production of malignancy in vitro. IV. The mouse fibroblast cultures and changes seen in the living cells", *Journal of the National Cancer Institute* 4, pp. 165–212 (1943) salts and supplemented with 10% inactivated (56° C. for 30 min) fetal calf serum, 100 units/ml penicillin, 100 μg/ml streptomycin, and 0.25 μg/ml amphotericin B. The serum used was negative for antibody to *T. gondii* in the Sabin-Feldman (Sabin, A. B., and Feldman, H. A., "Dyes as microchemical indicators of a new immunity phenomenon affecting a protozoan parasite (Toxoplasma)." *Science* 108, pp. 660–663 (1948)) dye test performed as described by Frenkel and Jacobs (Frenkel, J. K. and Jacobs, I., "Ocular toxoplasmosis", *Archives of Ophthal-* mology 59, pp. 260-279 (1958)). The cultures were incubated under 5% $CO_2$ in plastic tissue culture flasks or in disposable glass roller bottles. Their medium was replaced twice weekly and the cultures were split 1:3 when confluent. All infections with *T. gondii* were carried out in the medium described above with the concentration of inactivated fetal calf serum reduced to 3%. At this serum concentration, confluent monolayer cultures maintained their normal morphology for at least two weeks.

*Toxoplasma gondii*, strain RH, was in the form of a mouse peritoneal exudate. This strain was cloned twice successively. The final product was designated as the wild type. This wild-type *T. gondii* was maintained in the laboratory by passage in tissue culture at 37° C. Massively infected monolayers were dispersed into their medium by mechanical scraping, and the resulting suspension of extracellular and intracellular parasites was diluted 5- to 300-fold into fresh cultures. Temperature-sensitive mutants of *T. gondii* were maintained by similar tissue culture passage at 33° C.

Both mutant and wild-type parasites were preserved by storage in sealed glass ampoules under liquid nitrogen. (Bollinger, R. O., Musallam, N. and Stulberg, C. S., "Freeze preservation of tissue culture propagated *Toxoplasma gondii*," *Journal of Parasitology* 60, pp. 368-369 (1974)). The medium used for freezing contained Eagle's (1955) minimal essential medium in Hanks' salts (Hanks, J. H., and Wallace, R. E., "Relation of oxygen and temperature in the preservation of tissues by refrigeration", *Proceedings of the Society for Experimental Biology and Medicine*, 71, pp. 196-200 (1949)) supplemented with 10% inactivated fetal calf serum, 5% glycerol, and 5% dimethylsulfoxide. The recovery of viable parasites was significantly improved by slowly reducing the concentration of these cryoprotective agents over a period of 30 min. after thawing.

Before massive infection and host cell lysis supervene, most of the parasites in an infected culture are intracellular. Accurate plaque titrations and the isolation of mutants require the use of extracellular parasites. These were prepared in one of two ways, either one of which yielded suspensions in which microscopic examination showed that more than 95% of the parasites were extracellular. Plaque assays of various preparations showed that 12 to 75% of the wild-type extracellular parasites were infectious. The comparable values for temperature sensitive mutants were 6 to 50%. In the first method, the medium of an infected monolayer was decanted and the cells were scraped from the plastic surface with a rubber-tipped glass rod. Vigorous pipetting served to disperse the cells in 1 ml of fresh medium that was then transferred to a 4 ml vial. The cells in this suspension were disrupted by three forced passages through a 27-gauge needle attached to a 5 ml syringe (Chaparas, S. D., and Schlesinger, R. W., "Plaque assay of *Toxoplasma* on monolayers of chick embryo fibroblasts", *Proceedings of the Society for Experimental Biology and Medicine*, 102, pp. 431-437 (1959)). In the second method, the medium of an infected culture was decanted and replaced with an equal volume of fresh medium. After ½ to 2 hr. incubation, the paraistes newly released by spontaneous lysis were collected by again decanting the medium. Nearly all of the infected and uninfected cells remained attached to the plastic culture vessel.

Published methods for the plaque titration of *T. gondii* under an agar overlay (Chaparas and Schlesinger (1959); Akinshina, G. T., and Zasukhina, G. D., Method of investigating mutations in protozoa (*Toxoplasma gondii*), *Genetika* 2, pp. 71-75, (1966); and Foley, V. L. and Remington, J. S., "Plaquing of *Toxoplasma gondii* in secondary cultures of chick embryo fibroblasts", *Journal of Bacteriology* 98, pp. 1-3 (1969)) were tested and it was concluded that a procedure using a liquid overlay was simpler and reliable. Human diploid fibroblast cells were grown to confluency in 25 $cm^2$ plastic tissue culture flasks. The medium was discarded and replaced with fresh medium containing 3% inactivated fetal calf serum. Suspensions of extracellular *T. gondii* were diluted in Eagle's (1955) minimal essential medium in Hanks' (Hanks and Wallace 1949) salts and 3% serum and small volumes of suitable dilutions were added to the flasks. The flasks were then incubated undisturbed for 4 to 7 days, at 37° or 40° C., or 9 to 14 days at 33° C. The infectious parasites produced irregularly shaped plaques that were 1-2 mm in diameter. The irregular shape is a consequence of the oriented growth of our human fibroblasts. Macroscopically visible secondary plaques were not observed unless the culture was disturbed early in the incubation period. The plaques were counted without the aid of staining through the use of oblique illumination and a dark background. Preliminary experiments showed that staining the infected monolayers with cyrstal violet did not reveal additional plaques that were uncounted in unstained preparations. The data from our titrations are recorded as plaque forming units (PFU).

Selection of mutants requires an efficient method of cloning. Linbro Disposo-Trays were employed that contain 96 flat-bottomed wells 7 mm in diameter. These wells were seeded with 0.1 ml of medium containing about $10^5$ cells and a small number of parasites, estimated to lie between 0.3 and 3 PFU per well. This estimation was based on a microscopic enumeration of the extracellular parasites corrected for the probable degree of infectivity. The microwell cultures were incubated in a glass jar that was gassed with 5% $CO_2$ and then sealed. After an appropriate interval, 1 week for incubation at 37° and 40° C. or 2 weeks at 33° C., each individual culture was examined with an inverted microscope and the location of wells containing but a single plaque was noted. The parasites in these wells were assumed to be a clone. This conclusion is likely to be valid, for the distribution of plaques among the wells corresponded closely to the expected Poisson distribution. Both the wild-type and the mutant strains were cloned twice to give added assurance of genetic purity.

To permit chemical mutagenesis, extracellular parasites were allowed to infect about 10% of the cells of a confluent monolayer. At the time of infection N-methyl-N'-nitro-N-nitrosoguanidine (Aldrich Chemical Company) was added to the medium at a concentration of 0.8 μg/ml. After 24 hr incubation at 33° C., the mutagen was removed by three rinses with medium and the cultures were incubated in fresh medium at 33° C. for two additional days. Extracellular parasites were then prepared from the resulting massively infected culture and used in the isolation of temperature-sensitive mutants.

The rate of growth of *T. gondii* in tissue culture was measured in two ways. In the first, intracellular parasites were released by passing a cell suspension through a 27 gauge needle as described above. The resulting extracellular parasites were pooled with those previously spontaneously released into the medium and the total infectivity was determined by a plaque titration. This procedure was repeated at regular intervals using replicate cultures, and the data from the resulting titrations were used to construct a growth curve. Since this method was cumbersome when the rates of growth of several mutants were simultaneously to be determined at different temperatures, we also used a procedure that depended on microscopic enumeration. Replicate cultures were infected with about $10^1$ PFU and incubated undisturbed. At intervals, the total number of parasites in the resulting microfoci of infection was counted. This enumeration was done using unstained cells under 300-fold phase-contrast magnification. The individual parasites of at least 50 foci per flask were counted when the average per focus was less than 80. At higher values, the parasites of only 25 foci were counted. At fewer than 200 parasites per focus, the results were highly reproducible and yielded exponential growth curves, except when temperature-sensitive mutants were studied at temperatures that were inhibitory to growth. When these two methods were used in replicate infected cultures they yielded exponential growth curves of the same slope.

2. Results

Permissive and Restrictive Temperatures

The first step in the isolation of temperature-sensitive mutants is setting the permissive and restrictive temperatures. To this end, the ability of the wild-type *T. gondii* to grow in a plaque assay at various temperatures was successful. Plaques were produced over the range of 30° to 41° C. Growth at such a high temperature has also been noted by Akinshina and Zasukhina (1966). 40° C. was chosen as the restrictive temperature to be sure that minor fluctuations of incubator temperature would not affect the growth of the wild-type parasite. For the permissive temperature 33° C. was chosen; a compromise between a desire to have as great a span as possible between the two temperatures and a desire for a relatively rapid plaque assay. The efficiency of plating, the ability of the wild-type *T. gondii* to make plaques, was not compromised at either extreme of temperature. Table 1 compares the PFU titer of a single preparation of extracellular wild-type *T. gondii* under standard conditions, 37° C., and at the permissive and restrictive temperatures that were established. The slower growth of *T. gondii* at 33° C. required a longer incubation for the assay but the resulting plaques, as shown in FIG. 1, were roughly the same size. Furthermore, the data of Table I shows that temperature had no significant effect on the plating efficiency of the wild-type *T. gondii*.

TABLE I

Efficiency of Plating of Wild Type
*Toxoplasma gondii* at Different Temperatures

| Temperature (C) | Plaques counted in quadruplicate flasks* | Average |
|---|---|---|
| 40 | 432, 423, 408, 396 | 415 |
| 37 | 404, 394, 423, 432 | 413 |
| 33 | 430, 429, 429, 412 | 425 |

*These plaques were enumerated early in the incubation period (4 days at 37° and 40° C. or 9 days at 33° C.) to allow the reliable counting of large numbers.

Mutagenesis

Treatment with chemical or physical mutagenic agents is generally an essential step in the isolation of mutants of eukaryotic cells. This is particularly true in the search for temperature-sensitive mutants which may have no selective advantage that can be exploited to eliminate the undesired wild-type organisms. Mutagenic agents should always be used sparingly to avoid the introduction of additional extraneous mutations that might subsequently complicate the genetic and physiological studies. N-methyl-N'-nitro-n-nitrosoguanidine was used because of its proven ability to induce temperature-sensitive mutations in cultured mammalian cells (Naha, P. M., "Temperature sensitive conditional mutants of monkey kidney cells", *Nature* (London) 223, pp. 1380–1381 (1969); Thompson, L. H., Mankovitz, R., Baker, R. M., Till, J. E. Siminovitch, L., and Whitmore, G. F., "Isolation of temperature-sensitive mutants of L-cells", *Proceedings of the National Academy of Sciences U.S.A.* 66, p. 377 (1970); Miess, H., and Basilico, C., "Temperature sensitive mutants of BHK-21 cells", *Nature (New Biology)* 241, pp. 13–14 (1972)). Under the conditions described in the Materials and Methods section, this potent mutagen did not have a markedly lethal effect on *T. gondii*. Once the N-methyl-N'-nitro-N-nitrosoguanidine was removed, the treated parasites grew as fast as those of the control culture and the yield was reduced only to one-fourth of the control. This relatively high rate of survival and brisk growth suggests that the chemical mutagenesis was relatively mild. At least 48 hr. of growth was allowed after the removal of the mutagen to allow phenotypic expression of any induced mutations. During this period of growth, the preexisting functional proteins would be diluted and replaced with newly synthesized defective proteins in those parasites containing an induced temperature-sensitive mutation.

Selection of Temperature-Sensitive Mutants

Mutagenized *T. gondii* were cloned by plaque formation at 33° C. in microwells as described in the Materials and Methods section. After 2 weeks' incubation the wells that contained single plaques were identified by low power microscopy. The cells of these singly infected wells were scraped from the plastic with sterile toothpicks and aliquots of the resulting suspensions were seeded into duplicate microwell trays already containing fresh human fibroblast cells. The duplicate cultures were incubated at 40° or 33° C. for 1 and 2 weeks, respectively, and then examined for growth of the added parasites. *Toxoplasma gondii* from the vast majority of the clones grew perfectly well at both temperatures and were discarded as wild types. However, as recorded in Table II, parasites from 1.4% of the mutagenized clones failed to grow at 40° C. although they destroyed the parallel infected cultures at 33° C. The pheno-type of these possible temperature-sensitive mutants was checked by repeating the infections at both temperatures, using parasites from the well incubated at 33° C. as the inoculum. The confirmed mutants were then recloned at 33° C. and massively infected cultures were stored in liquid nitrogen. The mutants are numbered serially from "ts-1" to "ts-7".

Many clones of unmutagenized wild-type *T. gondii* were also examined for the presence of spontaneous temperature-sensitive mutants. Table II records the negative results of this search. The apparent increased frequency of temperature-sensitive mutants after chemical mutagenesis is significant at the $P < 0.01$ level, suggesting that N-methyl-N'-nitro-N-nitrosoguanidine is mutagenic for *T. gondii*.

TABLE II

Frequency of Temperature-Sensitive Mutants of *Toxoplasma gondii* in Mutagenized and Unmutagenized Cultures

| Preliminary treatment of *T. gondii* | Number of clones tested | Number of mutants isolated | Mutants[a] (%) |
|---|---|---|---|
| N—methyl-N'—nitro-N—nitrosognanidine[b] | 486 | 7 | 1.4 |
| None | 541 | 0 | 0 |

[a] The difference between the mutagenized and the unmutagenized clones is significant at the $P < 0.01$ level using the chi-squared test and one degree of freedom.
[b] The treatment is described in the Materials and Methods section.

In accordance with the invention, it has now been discovered that a specific mutant developed as described above (i.e., "ts-4") has particular utility for purposes of immunization of mammals without attendant chronic infection. A series of tests demonstrating the efficacy of the "ts-4" mutant in this context is presented below.

Inoculation Tests and Results

A variety of tests were performed on laboratory rabbits, squirrel monkeys and hamsters to determine the immunological activity and persistence of vaccines including the "ts-4" mutant described above. In certain additional tests, other infectious strains or antigens (i.e., RH, T-1, T-45 and killed Toxoplasma antigen (tAg) in Freund's complete adjuvant) were employed. The "ts-4" mutant was propagated in human foreskin fibroblasts in medium RPMI-1640 with 10% heat inactivated fetal calf serum and 100 μ/mcg/ml penicillin-streptomycin at 35°–37° C. in an atmosphere of 5% $CO_2$ in air, until inoculated. The remaining strains were maintained by serial passage of tachyzoites in mice.

Relevant additional details with respect to the tests are set forth below:

TEST 1

In this test laboratory rabbits were inoculated subcutaneously with about $10^4$ "ts-4" tachyzoites in 9% saline solution, and were challenged after two and ten months with the RH strain (which is the "parent" strain of the "ts-4" mutant). The results of this test are set forth in Table III. This test demonstrates that the "ts-4"-containing vaccine is effective for immunization of rabbits. The data also demonstrates that better survival of the rabbits is obtained if they are vaccinated in the ear, as opposed to flank vaccination. It is believed that these results were obtained because of the temperature-sensitive nature of the "ts-4" mutant, and the fact that the rabbits' ears are somewhat cooler than their main bodies. Thus, it is postulated that inoculations in ears or other lower temperature body appendages may give better immunity.

TABLE III

Tests for Persistence of Immunity in Rabbits

| | "ts-4" Vaccinated[b] | | |
|---|---|---|---|
| Challenge[a] | Flank | Ear | Controls |
| 2 months | | | |
| $10^7$ tachyzoites | s[c] | s | 10[d], 10 |
| $10^5$ tachyzoites | s | s | 12, s |
| $10^3$ tachyzoites | s | s | 12, 14 |
| 10 months | | | |
| $10^7$ tachyzoites | 8 | s, s | 12, 18 |
| $10^5$ tachyzoites | 9 | s | 11, 14 |

TABLE III-continued

Tests for Persistence of Immunity in Rabbits

| | "ts-4" Vaccinated[b] | | |
|---|---|---|---|
| Challenge[a] | Flank | Ear | Controls |
| $10^3$ tachyzoites | — | s | 10, 14 |

[a] Challenges employed RH strain of *T. gondii* injected into flanks
[b] Subcutaneous (sc) flank injections comprising $10^4$ ts-4 tachyzoites in 9% saline solution.
[c] s = animal survived
[d] Day of animal death (after challenge)

TEST 2

In this test squirrel monkeys were challenged at forty-one and fifty-six days after "ts-4" inoculation. The results of this test are set forth in Table IV. It will be noted that better survival is obtained where two inoculations are given, as opposed to only a single inoculation; however, the effectiveness of the "ts-4" vaccine in generating immunity is manifest.

TABLE IV

Pathogenic Challenge of Squirrel Monkeys

| "ts-4" inoculation[1] | Day of[2] Challenge | Route | Fraction Survival | Unvaccinated Controls |
|---|---|---|---|---|
| once | 41 | sc | ½ | 0/2 |
| twice[3] | 56 | sc | 1/1 | — |

[1] Subcutaneous (sc) flank injections comprising $10^4$ ts-4 tachyzoites in 9% saline solution.
[2] Days after last inoculation, using T-1 strain of *T. gondii*, $10^4$ tachyzoites, flank injected.
[3] Second injection occurred 27 days after first injection.

TEST 3

In this test hamsters were injected with various infectious strains of *T. gondii*, in order to determine the pathogenicity thereof. It will be noted in this regard that the "ts-4" strain was completely non-pathogenic, as opposed to the RH and T-1 strains which resulted in a high proportion of hamster deaths (see Table V).

TEST 4

In this test hamsters were again vaccinated with the various Toxoplasma strains, and weight gains or losses were recorded. The purpose of this test was to determine whether the "ts-4" vaccine gave rise to non-lethal illnesses in the hamsters. As the results of Table VI demonstrate, the weight gains recorded with respect to the "ts-4" inoculated hamsters are very close to those of the control hamsters, and it was therefore deduced that the "ts-4" vaccine did not cause debilitating illness in the hamsters (see Table VI).

TEST 5

In this test hamsters were inoculated with "ts-4" vaccine, and after four weeks the hamsters were sacrificed. Various organs of the hamsters were then ground and put into saline solution and subinoculated ip into mice. Dye test titers of the mice demonstrated that the antibody count was essentially zero, this occurring four weeks after the subinoculation. The mice were then challenged with the virulent RH *T. gondii* strain, with the result that none of the mice survived. The lack of antibody development and of immunity in the recipient mice demonstrates that the "ts-4" vaccination of hamsters does not lead to chronic infection of the hamster organs (see Table VII).

TEST 6

TABLE V

Survival Fraction and Mean Day of Death of Hamsters (60–70 g) Infected with Different Toxoplasma Strains

| Infection Strain | Injected number of tachyzoites | | | | | | |
|---|---|---|---|---|---|---|---|
| | $3.5 \times 10^0$ | $3.5 \times 10^1$ | $3.5 \times 10^2$ | $3.5 \times 10^3$ | $3.5 \times 10^4$ | $3.5 \times 10^5$ | $3.5 \times 10^6$ |
| RH | $1/5^{a,b}$ (12.0)$^c$ | 0/5 (11.2) | 0/5 (10.6) | 0/6 (9.5) | 0/4 (8.3) | ND | ND |
| T-1 | $1/5^a$ (16.3) | $1/5^a$ (16.8) | 0/5 (13.8) | 0/5 (15.4) | 0/5 (15.8) | 0/5 (14.6) | 0/5 (13.3) |
| T-45 | ND$^d$ | ND | ND | 5/5 | 5/5 | 5/5 | 5/5 |
| ts-4 | 5/5$^e$ | 4/4 | 4/4 | 6/6 | 6/6 | 6/6 | 3/3 |

[a]Survivor dye test for antibodies negative.
[b]Number survivors/number in group.
[c]3/5 survivors dye test for antibodies negative.
[d]ND = not done.
[e]Mean day of hamster deaths.

TABLE VI

Effect of Toxoplasma Infection or Vaccination on Body Weight of Hamsters

| Toxoplasma strain | n$^a$ | 0$^b$ | Week 1 | 2 | 3 | 4 |
|---|---|---|---|---|---|---|
| RH | 8 | 69.0 ± 4.7 | −2.2%$^c$ | — | — | — |
| T-1 | 5 | 129.5 ± 10.1 | ND$^d$ | −13.3% | −31.5% | — |
| | 6 | 148.3 ± 7.4 | ND | −45.4 | — | — |
| | 4 | 114.2 ± 9.6 | ND | −36.8 | — | — |
| T-45 | 7 | 116.6 ± 6.9 | −5.8 | −10.1 | ND | +1.5 |
| ts-4 | 5 | 81.4 ± 3.8 | +10.1 | +22.0 | ND | +42.0 |
| (tAg-FCA)$^e$ | 10 | 69.8 ± 3.3 | ND | ND | ND | +44.7 |
| | 6 | 69.0 ± 2.6 | ND | ND | ND | +40.4 |
| Saline Control | 5 | 71.2 ± 5.6 | +11.5 | +25.5 | ND | +46.6 |

[a]Number of hamsters per group.
[b]Mean group weight in grams the day of challenge or vaccination.
[c]Percent change from weight on day of vaccination.
[d]ND = not done.
[e]tAg-FCA = nonviable Toxoplasma antigen in Freund's complete adjuvant.

In this test hamsters vaccinated with "ts-4" mutant were challenged after various periods of time with the virulent RH and T-1 *T. gondii* strains. It will be observed (see Table VIII) that the survival rates of the vaccinated hamsters, as opposed to the controls, was very high. The vaccination of the hamsters occurred only once, and it is believed that complete immunity for all the subjects could be obtained by a double inoculation.

TEST 7

In this test respective groups of hamsters were vaccinated with RH, T-45, T-1, ts-4, and tAg in FCA. The first three vaccinations required chemoprophylaxis with sulfadiazine. This involved adding sulfadiazine to the hamsters' drinking water (30–60 mg/100 ml) for three to four weeks after inoculation, in order to permit the survival of these subjects. The "ts-4" vaccine did not require chemoprophylaxis, nor did those hamsters inoculated with tAg in FCA. As noted in Table IX, a high percentage of the hamsters inoculated with live vaccine (i.e, all but those inoculated with tAg in FCA) survived the RH strain challenge. In the case of "ts-4", it is believed that 100% survival can be obtained using two separate, spaced in time vaccination doses.

TABLE VII

Subinoculation of Tissues from ts-4 Vaccinated Hamsters into Mice to Determine the Presence of Persistent Organisms in Hamsters

| Subinoculation material | Donors No. of Hamsters | Recipients No. of Mice | Dye test Titer | RH Challenge of Mice | |
|---|---|---|---|---|---|
| ts-4 vaccinated hamsters:$^a$ | | | | | |
| Lung | 8 | 8 | <2 | 7.9$^c$ | 0/8$^d$ |
| Liver | 8 | 8 | <2 | 8.0 | 0/8 |
| Spleen | 8 | 8 | <2 | 7.6 | 0/8 |
| Kidney | 8 | 8 | <2 | 7.9 | 0/8 |
| Adrenal | 8 | 8 | <2 | 7.6 | 0/8 |
| Heart | 8 | 8 | <2 | 8.0 | 0/8 |
| Pancreas | 8 | 8 | <2 | 7.7 | 0/8 |
| Brain | 8 | 8 | <2 | 8.4 | 0/8 |
| Uterus | 8 | 8 | <2 | 8.1 | 0/8 |
| Skeletal muscle & injection site for ts-4 | 8 | 8 | <2 | 8.2 | 0/8 |
| Controls for subinoculation | | | | | |
| Normal hamster brain | 4 | 4 | <2 | 7.3 | 0/4 |
| ts-4 tachyzoites (n = $10^6$)$^b$ | 0 | 4 | 64 | 8.0 | 1/4 |
| ts-4 tachyzoites (n = $10^3$)$^b$ | 0 | 4 | 1,000 | 7.0 | 3/4 |

[a]Hamsters vaccinated with $10^4$ ts-4, sc, 4 weeks previously.
[b]ts-4 injected into mice sc.
[c]Mean day of death, sc challenge was 2 weeks after subinoculation of tissue.
[d]Number of survivors/number in group.

TABLE VIII

Toxoplasma Challenge of ts-4 Vaccinated Hamsters

| Vaccine | Challenge Strain | Challenge dose and time of challenge after vaccination | | | | |
|---|---|---|---|---|---|---|
| | | 2 wk - $10^3$ | 4 wk - $10^3$ | 8 wk - $10^3$ | 16 wk - $10^3$ | 24 wk - $10^3$ |
| ts-4 | RH | 6/6$^a$ | 6/6 | 4/5 (10.0) | 5/5 | 3/5 (13.5 ± .7) |
| None | RH | 0/7 (9.8 ± .4)$^b$ | 0/6 (9.5 ± 1.2) | 0/5 (10.0 ± 1.2) | 0/4 (9.7 ± .5) | 0/5 (9.2 ± .4) |
| ts-4 | T-1 | ND | ND | ND | 6/6 | ND |

TABLE VIII-continued

Toxoplasma Challenge of ts-4 Vaccinated Hamsters

| Vaccine | Challenge Strain | Challenge dose and time of challenge after vaccination | | | | |
|---|---|---|---|---|---|---|
| | | 2 wk - $10^3$ | 4 wk - $10^3$ | 8 wk - $10^3$ | 16 wk - $10^3$ | 24 wk - $10^3$ |
| None | T-1 | ND | ND | ND | 0/2 (15.0 ± 0) | ND |

[a]Number of survivors/number challenged.
[b]Mean day of death ± 1SD.

TABLE IX

Percent Survival of Hamsters Following RH Strain Challenge

| Vaccine | Type of infection or vaccine | Time of Challenge after infection or vaccination | Percent Survival (5–6 per group) |
|---|---|---|---|
| RH[a] | Persistent | 2, 4, 6, 16, or 24 wk | 100% |
| T-45 | Persistent | 4, 16, or 24 wk | 100% |
| T-1[a,b] | Persistent | 4 or 24 wk | 100% |
| ts-4 | Non persistent | 2, 4, 16 wk | 100% |
| | | 8 and 24 wk | 70% |
| [d]tAg in Freund's complete adjuvant | killed vaccine | 4 wk | 0% |
| None | None | 2, 4, 8, 16, 24[c] | 0% |

[a]Sulfadiazine (90 mg %) chemotherapy was given with the vaccination.
[b]Survivors of T-1 infection.
[c]Normal control hamsters infected at time vaccinated hamsters were challenged.
[d]Nonviable Toxoplasma antigen.

TEST 8

This test was designed to determine the amount of time required for the onset of immunity after "ts-4" vaccination of hamsters and mice. In this test, the subject animals were inoculated and challenged on the listed days thereafter with RH *T. gondii* (see Table X). It will be noted that the hamsters achieved virtually complete immunity after four days, whereas in mice the period required for the development of immunity was somewhat longer.

TEST 9

In this test groups of hamsters were inoculated with the listed strains of *T. gondii* or mutants thereof, with the first three groups requiring sulfadiazine chemoprophylaxis for a period of four weeks in order to ensure survival. Challenge occurred 112 days after inoculation, by feeding the hamsters Toxoplasma-infected meat. Inasmuch as ingestion of infected meat is the usual means of infection, this test demonstrates that "ts-4" vaccination provides a very high degree of immunity against this usual infective route.

TEST 10

In this test hamsters were inoculated with various doses of "ts-4", and the buildup of immunity in the animals was thereafter monitored by dye test titer and RH strain challenge. The challenge occurred 14 days after inoculation. As the results of Table XII indicate, complete immunity against challenge in the hamsters resulted with a dose as small as 20 tachyzoites in saline solution.

TABLE X

Onset of Immunity to RH Strain Challenge Following -4 Vaccination

| Days of Challenge | Mean Days of Death | | Percent Survival (5–6 per group) | | Causes of Death[a] Days of Death |
|---|---|---|---|---|---|
| | Hamsters | Mice | Hamsters | Mice | |
| 0[b] | 9.5 .5 | 8.6 ± 0.5 | 0 | 0 | Pneumonia (9, 10) |
| 0 | 10.0 1.2 | 8.8 ± 0.8 | 0 | 0 | Pneumonia (8, 10, 11) |
| 2 | 12.5 3.8 | 8.8 ± 0.9 | 20 | 0 | Pneumonia (10, 12); Encephalities (18) |
| 3 | 23.5 7.5 | ND | 60 | — | Encephalities (18, 29) |
| 4 | — | 7.0 ± 0.7 | 100 | 0 | — |
| 5 | — | ND | 100 | — | — |
| 6 | — | 10.2 ± 2.8 | 100 | 0 | — |
| 8 | 13.0 | 12.2 ± 2.2 | 83 | 20 | Pneumonia (13) |
| 10 | — | 11.7 ± 0.6 | 100 | 60 | — |
| 14 | — | 8.0 | 100 | 75[c] | — |
| 21 | — | 19.0 | 100 | 83 | — |

[a]For hamsters only; the cause of pneumonia or encephalitis was Toxoplasma.
[b]No vaccine.
[c]4 mice in this group.

TABLE XI

Immunity to Oral Challenge with T-1 Toxoplasma Bradyzoites = meat

| | Number of Deaths per Number per Group | Mean Day of Death | challenged of survivors[b] |
|---|---|---|---|
| Hamsters | | | |
| RH chronic | 0/12 | — | all survive |
| T-1 chronic | 0/5 | — | " |
| T-45 chronic | 0/4 | — | " |
| ts-4 vaccinated | 0/12 | — | " |
| Normal | 6/9 | 7.5 ± 1.4[a] | died |
| Mice | | | |
| Normal | 5/5 | 8.0 ± 1.9 | died |

[a]Three survivors dye tests titers >1,000, 2 weeks.
[b]$10^5$ RH tachyzoites, administered sc.

TABLE XII

The Effect of Different Doses of ts-4 on the Establishment of Protective Immunity and Antibody Response 2 weeks After Vaccination of Hamsters and Mice

| Counted dose of ts-4 | Dye test titer[a] | Hamsters RH challenge[b] |
|---|---|---|
| 2 × $10^4$ | 64,000 | 4/4 |
| × $10^3$ | 16,000 | 4/4 |
| × $10^2$ | 16,000 | 4/4 |
| × $10^1$ | 32,000 | 4/4 |
| | 8,000 | |
| | 4,000 | |
| | 4,000 | |
| × $10^0$ | 16,000 | (9.3)c |
| | 4,000 | |
| | <4 | |
| | <4 | |
| | <4 | |
| × $10^{-1}$ | <2 | 0/4 (9.2) |

TABLE XII-continued

The Effect of Different Doses of ts-4 on the Estabilishment of Protective Immunity and Antibody Response 2 weeks After Vaccination of Hamsters and Mice

| Counted dose of ts-4 | Dye test titer[a] | Hamsters RH challenge[b] |
|---|---|---|
| None | <2 | 0/5 (9.2) |

[a]Dye test titers result of test on pool of .1 ml serum from each animal in group. Titers from hamsters given $10^0$, $10^1$ were individually determined.
[b]Number of survivors/number challenged with $10^3$ RH strain, administered sc two weeks after vaccination.
[c]Mean day of death.

We claim:

1. A method of immunizing man, cattle, sheep, goats, birds on zoo mammals against *Toxoplasma gondii*, comprising the step of administering thereto by subcutaneous injection an amount of a mutant of *Toxoplasma gondii* for developing immunity to *Toxoplasma gondii* challenge without concomitant chronic *Toxoplasma gondii* infection, said mutant being designated ts-4 by the American Type Culture Collection and having accession number 40050.

2. The method of claim 1, wherein said mutant is injected at a level of at least about 20 tachyzoites.

3. The method of claim 1, wherein man is immunized.

* * * * *